United States Patent
DePue et al.

(10) Patent No.: US 7,054,009 B2
(45) Date of Patent: May 30, 2006

(54) METHOD AND APPARATUS FOR ULTRA-HIGH SENSITIVITY OPTICAL DETECTION OF BIOLOGICAL AND CHEMICAL AGENTS

(75) Inventors: Marshall T. DePue, San Mateo, CA (US); Tong Xie, San Jose, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 409 days.

(21) Appl. No.: 10/698,589

(22) Filed: Oct. 31, 2003

(65) Prior Publication Data

US 2005/0094150 A1    May 5, 2005

(51) Int. Cl.
   *G01N 21/00* (2006.01)
   *G01N 21/41* (2006.01)
   *G01N 21/47* (2006.01)
(52) U.S. Cl. .................... 356/437; 356/440; 422/82.09
(58) Field of Classification Search .............. 356/437, 356/432
   See application file for complete search history.

(56) References Cited

U.S. PATENT DOCUMENTS

| | | | |
|---|---|---|---|
| 4,297,035 A | 10/1981 | Bjorklund | |
| 5,506,685 A | 4/1996 | Grasdepot | |
| 5,835,231 A | 11/1998 | Pipino | |
| 6,515,749 B1 * | 2/2003 | Pipino | ........................ 356/440 |

2002/0122179 A1    9/2002    Pipino

OTHER PUBLICATIONS

Pipano, A.C.R. et al., "Evanescent Wave Cavity Ring-Down Spectroscopy with a Total-Internal-Reflection Minicavity", American Institute of Physics, New York, US vol. 68, No. 8, Aug. 1, 1997, pp. 2978-2989.

Haes, Amanda J. et al., "A Nanoscale Optical Biosensor: Sensitivity and Selectivity of an Approach Based on the Localized Surface Plasmon Resonance Spectroscopy of Triangular Silver Nanoparticlaes", J.Am.Chem.Soc, 2002, 124, pp. 10596-10604.

Bjorklund, Gary C., "Frequency-Modulation Spectroscopy: A New Method for Measuring Weak Absorptions and Dispersions", Optics Letters, vol. 5, No. 1, Jan. 1980, pp. 15-17.

Engelin, Richard et al., "Phase Shift Cavity Riing Down Absorption Spectroscopy", Chemical Physics Letters, 262, Nov. 8, 1996, pp. 105-109.

Pipino, Andrew C.R., "Evanescent Wave Cavity Ring-Down Spectroscopy with a Total-Internal-Reflection Minicavity", Rev.Sci.Instrum. vol. 68, No. 8, Aug. 1997, pp. 2978-2989.

Armani, D.K., "Ultra-High-Q Toroid Microavity on a Chip", Letters to Nature, vol. 421, Feb. 2003, pp. 925-928.

* cited by examiner

*Primary Examiner*—Layla G. Lauchman
*Assistant Examiner*—Roy M. Punnoose

(57) ABSTRACT

Combining the approaches of cavity ring down spectroscopy with surface plasmon resonance spectroscopy allows creation of an ultra-high sensitivity apparatus to detect extremely low concentrations of chemicals and biomolecules.

20 Claims, 4 Drawing Sheets

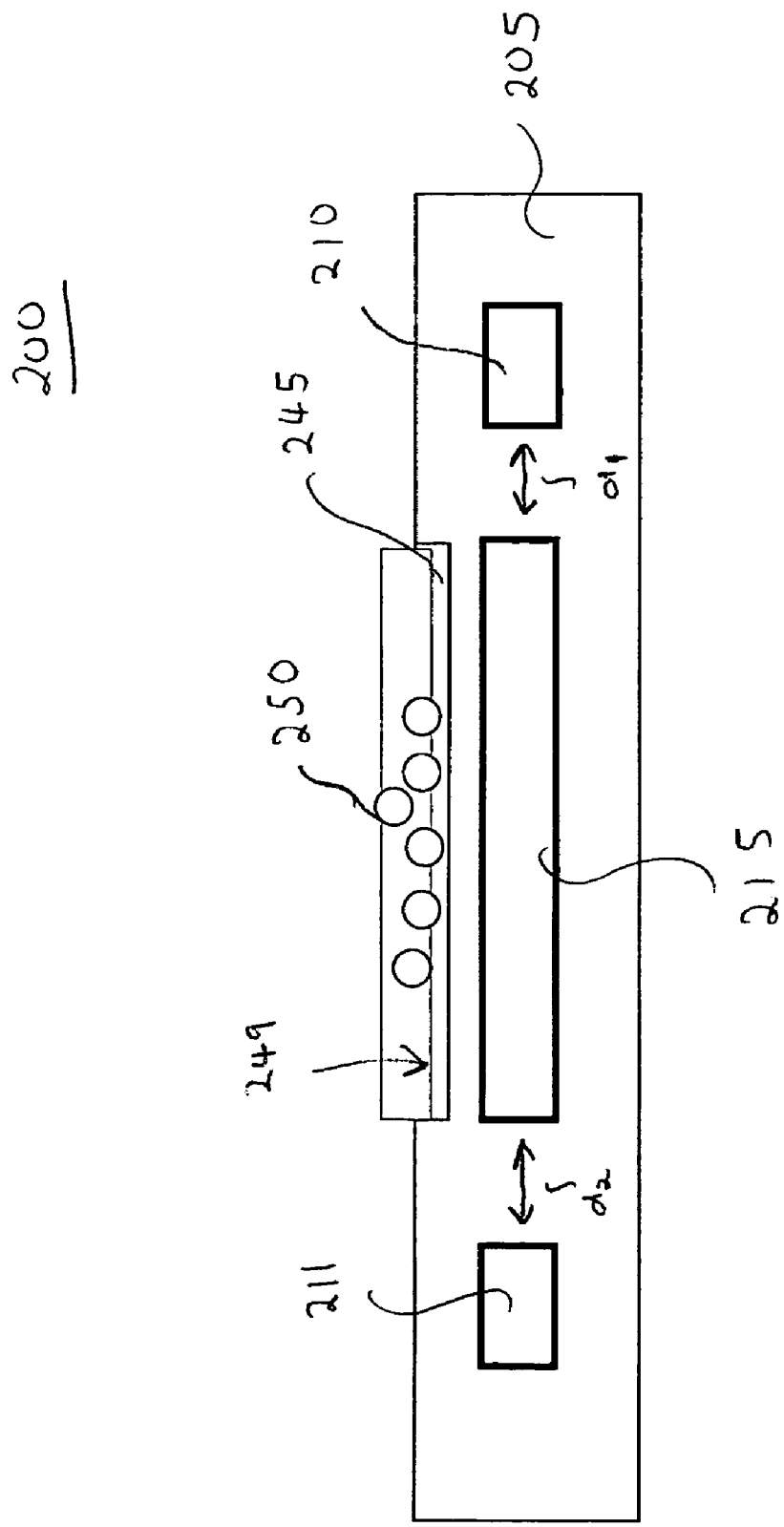

METHOD AND APPARATUS FOR ULTRA-HIGH SENSITIVITY OPTICAL DETECTION OF BIOLOGICAL AND CHEMICAL AGENTS

BACKGROUND OF THE INVENTION

Conventional approaches to optical detection of chemical reactions using surface plasmon resonance typically relies upon a measurement of the optical intensity of the laser light absorbed by a surface excitation in a thin metal layer. A surface plasmon is a localized oscillation of free electrons on the metal surface. The light absorption characteristics of the surface plasmon resonance depend sensitively on the dielectric constant near the metal surface. A chemical reaction occurring at the metal surface modifies the local dielectric environment resulting in a change in the absorption characteristics of the resonance. For further details, see for example, Duyne et al., Journal of the American Chemical Society 2002, 124, 10596–10604.

Present techniques rely on measuring the fraction of incident optical power that is absorbed by the surface plasmon resonance. High sensitivity measurements are typically difficult to make using direct intensity detection, see for example, U.S. Pat. No. 5,506,685. In particular, measurements of optical intensity are directly sensitive to laser intensity noise. Near shot-noise limited measurements may be made by monitoring the phase of the absorbed light as described in Bjorkland et al., Optical Letters, 5, 15, 190 and U.S. Pat. No. 4,297,035, for example. These phase techniques typically require phase modulation of the incident optical field and are typically complex and costly.

SUMMARY OF THE INVENTION

In accordance with the invention, ring-down spectroscopy techniques are combined with surface plasmon resonance detection to allow ultra-sensitive chemical analysis in conjunction with an optical source. This allows improved chemical sensors with higher sensitivities than conventional surface plasmon techniques. The enhanced sensitivity allows use of smaller sample sizes and the ability to detect smaller concentrations of the chemical substances of interest.

BRIEF DESCRIPTION OF THE DRAWINGS

FIG. 2b shows a side view of an embodiment in accordance with the invention.

DETAILED DESCRIPTION OF THE INVENTION

Figure 1A:
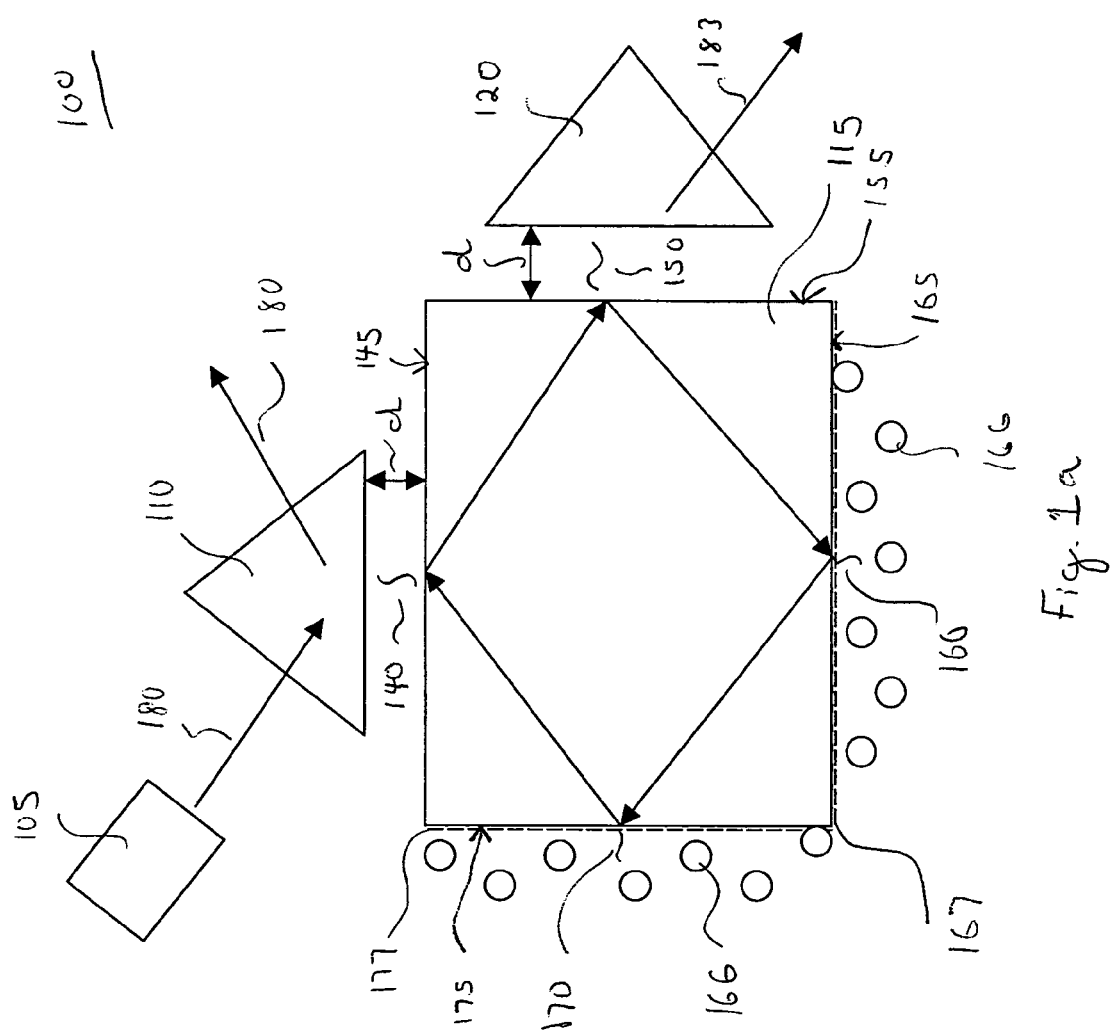
FIG. 1a shows an embodiment in accordance with the invention using discrete optics.

FIG. 1 shows cavity ring-down spectrophotometer (CRDS) 100 in an embodiment in accordance with the invention. CRDS 100 uses total internal reflection (TIR) to improve the cavity efficiency and provides for the presence of evanescent waves 140, 150, 160 and 170. While ring cavity resonator 115 in FIG. 1 has a square shape other polygonal shapes such as hexagons or octagons, for example, may also be used as a ring cavity resonator in embodiments in accordance with the invention. Polygonal shapes with more sides such as hexagonal and octagonal ring cavity resonators typically are more difficult to fabricate.

A stable ring cavity resonator supports one or more low-diffraction modes which are self-reproducing after one round-trip pass through the resonator. However, ring cavity resonator 115 is borderline unstable if all faces 145, 155, 165 and 175 are plane parallel. If one of faces 145, 155, 165 and 175 is a convex face, stability is induced and diffraction losses are significantly reduced. Typically, either face 145 or 155 is chosen to be convex in accordance with the invention.

A typical material for CRDS 100 in the near-infrared is fused-silica. In mid infrared applications involving vibrational spectroscopy, fluoride-doped glasses have low bulk attenuation coefficients of $L_{bulk} \sim 1 \cdot 10^{-7}$/cm or less. This low bulk attenuation has the potential for permitting individual molecule detection by cavity ring-down spectroscopy as described by Pipino et al. in "Evanescent wave cavity ring-down spectroscopy with a total-internal-reflection minicavity", in Reviews of Scientific Instruments, 68, 8, Aug. 1997, p. 2978, incorporated by reference in its entirety. The ultimate sensitivity of CRDS 100 and CRDS 200 (see FIGS. 2a, 2b) is determined by the magnitude of the intrinsic cavity losses and the relative uncertainty in the measured photon decay time. To achieve ultra-high sensitivity detection, cavity loss is reduced and photon decay time needs to be measured with high precision. Techniques such as superpolishing applied to CRDS 100 allows fabrication of ultralow-loss optics to reduce loss in ring cavity resonator 115 and allow for large cavity quality (Q) factors with correspondingly low photon decay times that may be digitized with high precision. In some embodiments in accordance with the invention, where the cavity Q is extremely high, the received optical power may be very small. Under such conditions, the well-known techniques of coherent detection, such as heterodyne detection may be used to detect such weak signals.

Direct coupling of free-space waves cannot typically be achieved when cavity modes are sustained totally by TIR. However, a consequence of TIR is the generation of evanescent waves 140, 150, 160, 170 which are required to satisfy the boundary conditions imposed by Maxwell's equations for light incident from a denser medium at an angle that exceeds the critical angle. The presence of evanescent waves 160 and 170 allows probing of region 166 and 177 in FIG. 1. Additionally, the broadband nature of TIR removes the bandwidth restrictions that are characteristic of the dielectric mirrors of non-TIR CRDS.

In accordance with the invention, tunable laser 105 is typically used to generate light pulse 180 which is totally reflected by totally reflecting prism 110 creating evanescent wave 140. Evanescent wave 140 excites the stable modes of TIR ring cavity resonator 115 through photon tunneling or frustrated total internal reflection. Hence, totally reflecting prism 110 is placed in close proximity to TIR cavity resonator 115 so that the evanescent field is phase matched to the modes of TIR cavity resonator 115. Similarly, totally reflecting prism 120 is placed in close proximity to TIR cavity resonator 115 to allow evanescent out coupling via totally reflecting prism 120 using evanescent wave 150.

Depending on the resonator geometry, the indices of refraction, the wavelength, and total round-trip loss, a gap width will exist where the coupling loss equals the total round-trip loss of TIR cavity resonator 115 and providing impedance matched coupling. For smaller gap widths, over coupling occurs which reduces the finesse (or Q) of TIR cavity resonator 115. For larger gap widths, coupling efficiency plateaus as the maximum finesse of TIR cavity resonator 115 is approached. Typically, for TIR cavity resonator 115, weaker coupling is preferred because it allows higher finesse. Weaker coupling results in lower light throughput, signal levels may be improved through multiple mode excitation or mode-matched cw excitation, as described, for example, by Mweijer and Engeln in Chemical Physics Letters, 262, 105, 1995.

The photon decay time in a monolithic, TIR cavity resonator with n facets such as TIR cavity resonator 115 is given by:

$$\tau(\omega) = \frac{t_r}{L_{bulk} + L_{surf} + L_{coupling} + L_{diff} + L_{nspec} + L_{plasmon}} \quad (1)$$

where the total intrinsic TIR cavity resonator loss is approximated by the sum of the round trip losses $L_i$ and the $L_{plasmon}$ term contributes during surface plasmon resonance detection.

Given an n-sided TIR cavity resonator with a refractive index $n_r$, the round-trip time $t_r$ is given by $$t_r = n_r L_n/c = 2n(n_r/c)r_0 \sin(\pi/n) \quad (2)$$

where $r_0$ is the inscribed-circle radius of the associated polygon and $L_n$ is the round trip physical path length, which approaches the limit $2\pi r_0$ as $n \to \infty$. The dependence of photon decay time on the size of the TIR cavity resonator is incorporated directly in $t_r$ and $L_{bulk}$, $L_{diff}$ depends on cavity size through stability factors and apertures associated with the finite facet dimensions. For a TIR cavity resonator fabricated from highly transparent material, the loss per pass due to bulk attenuation is given by:

$$L_{bulk} = 2\alpha r_0 n \sin(\pi/n) \quad (3)$$

where $\alpha$ is the bulk attenuation coefficient.

If bulk attenuation is sufficiently small (~500 ppm/pass), surface scattering losses may be significant. From scalar diffraction theory, the reduction in the mean specularly reflected intensity per round trip is given by:

$$L_{surf} \approx \left(\frac{4\pi n_i \sigma_{rms} \sqrt{n} \sin(\pi/n)}{\lambda_0}\right)^2 \quad (4)$$

where $\sigma_{rms}$ is the root-mean-square surface roughness, $\lambda_0$ is the vacuum wavelength and n is the number of faces of the n-sided TIR cavity resonator.

The loss term $L_{coupling}$ represents the loss due to input and output coupling on faces 145 and 155 due to photon tunneling or frustrated total internal reflection. The loss term $L_{nspec}$ refers to loss from nonspecular reflection. Nonspecular reflection arises from the finite nature of the lightbeam diameter which has associated with it a distribution of wave vectors in the angular spectrum, with inverse proportionality between beam diameter and spectral width. Each component in the angular spectrum experiences a different phase and amplitude modification resulting in nonspecular reflection. This loss mechanism is typically insignificant with respect to other sources of loss.

Faces 165 and 175 of TIR cavity resonator 115 are the locations of thin metal layers 167 and 177 used for the surface plasmon resonance (SPR) detection. A plasmon is an inhomogenous solution to the electromagnetic wave equation that is highly sensitive to the local dielectric environment. Thin layer of metal (typically silver or gold) layers 167 and 177, typically having a thickness on the order of nanometers, are deposited on faces 165 and 175 in accordance with the invention. Silver typically suffers from long term stability problems due to oxidation. The p-polarized component of evanescent waves 160 and 170 interacts with the free electrons on the surface of thin metal layers 167 and 177.

A surface plasmon resonance is formed when the lightwave in TIR cavity resonator 115 is in a state of well-defined momentum determined by polarization, wavelength and incident angle. For plasmon excitation by the lightwave to occur, the wavevector of the light wave component parallel to the thin metal layer and the wavevector of the plasmon need to be equal. The wavevector of the plasmon depends on the refractive indices of the thin metal layer and the sample medium (typically the transducing layer and the analyte). When the surface plasmon resonance is excited, the loss increases because light is resonantly absorbed to drive the electron charge density oscillation. The photon decay time $\tau(\omega)$ (see Eq. (1)) is shorter the greater the plasmon loss, $L_{plasmon}$, and is a direct measurement of the plasmon absorption coefficient. For a TIR cavity resonator:

$$L_{plasmon} = (n-2)\sigma_{plasmon}(\omega) \int_0^d N_{plasmon}(\xi)\delta(\xi-h)\,d\xi \quad (5)$$

where n is the number of sides of TIR cavity resonator, d is the effective sampling depth of the evanescent wave, $\sigma_{plasmon}(\omega)$ is the absorption cross-section as a function of frequency for the surface plasmon, h is the thickness of the thin metal layer, $N(\xi)_{plasmon}\delta(\xi-h)$ is the number density of plasmons and the dirac delta function indicates that plasmons are excited only at the outer surface of the thin metal layer at $\xi=h$. Note that if d<h, $L_{plasmon}=0$. For TIR cavity resonator 115, n=4 and the expression can be rewritten as $$L_{plasmon} = \frac{2\sigma_{plasmon} N_{plasmon}}{(\omega - \omega_{plasmon})^2} \quad (6)$$

where $\sigma_{plasmon}(\omega)$ has been separated into a constant term $\sigma_{plasmon}$ and a frequency dependent Lorentzian absorption lineshape with resonant frequency at $\omega=\omega_{plasmon}$.

A sample medium relating to a chemical or biological reaction may be sensed using CRDS 100. For example, in accordance with the invention, a transducing layer, typically having a thickness of about 1 μm, is deposited onto thin metal layers 167 and 177 on faces 165 and 175, respectively. Transducing layers are typically formed from polymers and applied using spin coating or dip coating techniques in chemical sensing applications. The transducing layer adsorbs or chemically reacts with the analyte or chemical to be detected.

In biosensing applications, the transducing medium is typically formed as a matrix or layer of biomolecules which are capable of binding the analyte molecules 166. Various biomolecular interactions may be used including antigen-antibody, receptor-ligand and hormone-receptor binding.

The presence of analyte 166 changes the local dielectric constant on faces 165 and 175. The change in local dielectric constant effects the plasmon absorption coefficient resulting in a change in the value of the photon decay time $\tau(\omega)$ through $L_{plasmon}$. The photon decay rate or ring down time is first measured for CRDS 100 in the absence of the analyte or chemical to be detected but with thin metal layers 167 and 177 and the transducing layers present. The light from tunable laser 105 excites a surface plasmon resonance and depending on the frequency, a certain fraction of the light is absorbed. The photon decay rate $\tau(\omega)$ of cavity resonator 115 and the finesse are inversely proportional to the fraction of light absorbed. Then faces 165 and 175 of CRDS 100 are exposed to analyte 166, the chemical or biological agent to be sensed. As analyte 166 interacts with the transducing layer, the local dielectric constant is modified in the vicinity of the surface plasmon. This effects the nature of the surface plasmon resonance: changes in the dielectric constant alter the plasmon absorption and resonance frequency. If more light is absorbed in the presence of analyte 166 leading to a decrease in the value of $\tau(\omega)$. The difference between the photon decay time in the absence and presence of analyte 166 is proportional to the concentration of analyte 166 through the plasmon loss term of Eq. (5).

Figure 1B:
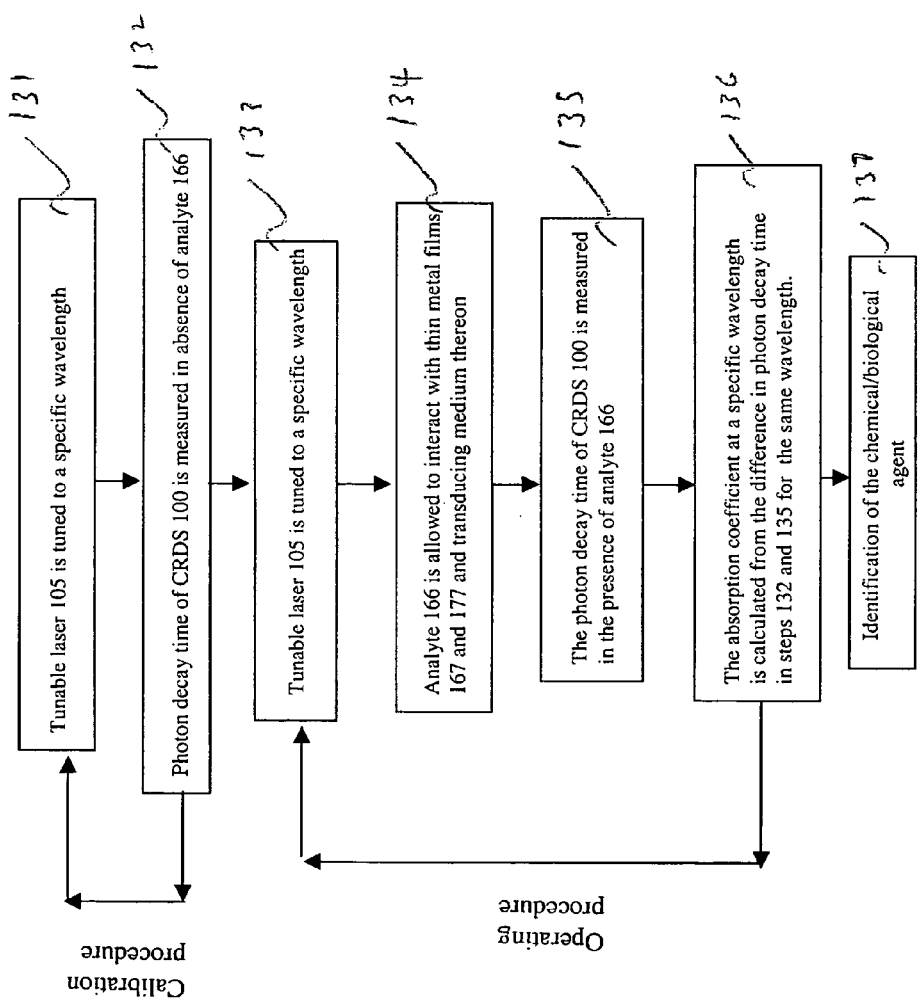
FIG. 1b shows a flow chart for a method in accordance with the invention.

FIG. 1b shows the steps for an embodiment in accordance with the invention for mapping the change in the surface plasmon resonance coefficient in the presence of analyte 166 as a function of the frequency of tunable laser 105. In step 131, tunable laser 105 is tuned to a specified wavelength $\lambda_1$. In step 132, the photon decay time of CRDS 100 is first measured in the absence of analyte 166. Optionally, step 131 may be repeated multiple times to obtain an average to reduce any noise. Steps 131 and 132 are repeated with the next wavelength $\lambda_i$ until CRDS 100 has been calibrated over the wavelength range $\lambda_1 \ldots \lambda_n$ of interest. In step 133, laser 105 is tuned to wavelength $\lambda_1$. In step 134, analyte 166 is allowed to interact with thin metal films 167 and 177 and the transducing layer on located each thin metal film 167 and 177. In step 135, the photon decay time for CRDS 100 is measured in the presence of analyte 166. Optionally, step 135 may be repeated multiple times to obtain an average to reduce noise. In step 136, the absorption coefficient at a particular wavelength is calculated from the difference in photon decay time of CRDS 100 at a particular wavelength in the absence of analyte 166 and in the presence of analyte 166. Steps 133 through 136 are repeated with the next wavelength $\lambda_i$ until the absorption coefficient as a function of wavelength has been mapped over the wavelength range $\lambda_1 \ldots \lambda_n$ of interest. In step 137 the chemical or biological is identified based on the results from step 136.

A difference in the photon decay rate typically indicates the presence of a particular chemical or biological agent, even at very low concentrations. Relative uncertainties in photon decay time of 0.2% are reported by Pipino et al. in "Evanescent wave cavity ring-down spectroscopy with a total-internal-reflection minicavity", in Reviews of Scientific Instruments, 68, 8, Aug. 1997, p 2978, enabling sensitivities on the order of parts per $10^{10}$ or better to be achieved. The accessibility to such high sensitivity measurements allows the presence of very low concentrations to be detected using ring-down techniques. Measurement of changes involves the measurement of a decay rate and therefore is not sensitive to laser intensity noise and is shot-noise limited. However, the photon decay must be sufficiently long such that accurate digitization of the decay curve can be obtained.

Figure 2A:
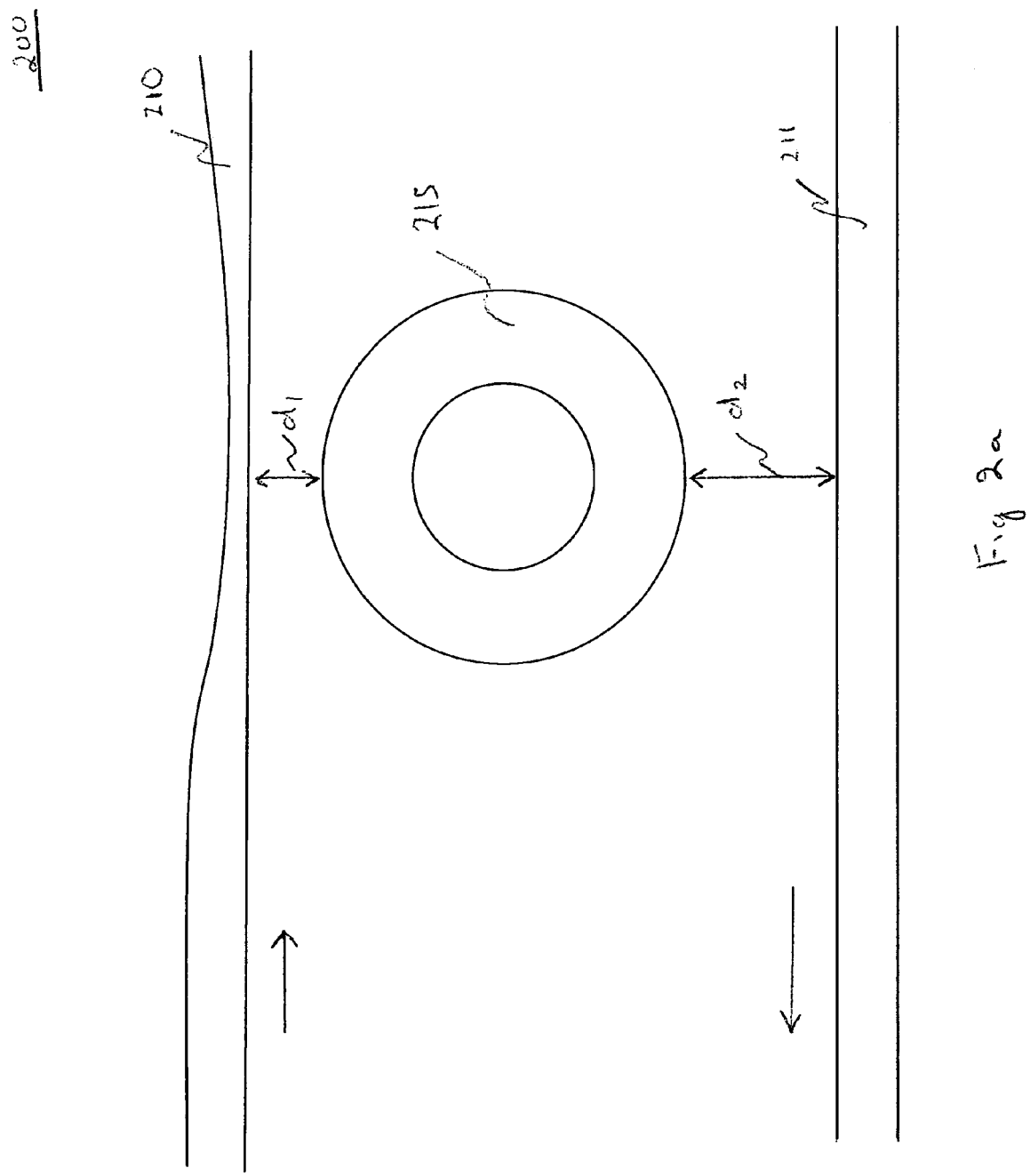
FIG. 2a shows a top view of an embodiment in accordance with the invention.

FIG. 2a shows a top view of planar cavity ring-down spectrophotometer (CRDS) 200 in accordance with the invention. Planar CRDS 200 is configured as a planar lightwave circuit allowing compact, cheap and integrated sensors and may be made using well-known methods adapted from the making of planar lightwave circuits. Planar waveguides 210, 211 and ring cavity resonator 215 are created in substrate 205 (see FIG. 2b), typically made from $SiO_2$. Note that waveguide 210 is adiabatically tapered to mode-match ring cavity resonator 215. This provides for low coupling loss while maintaining high finesse. Light from typically a tunable laser source propagates in planar waveguide 210 and couples to ring cavity resonator 215 via an evanescent wave that excites the stable modes of ring cavity resonator 215 through photon tunneling or, equivalently, frustrated total reflection. Hence, planar waveguide 210 is separated from ring cavity resonator 215 by gap $d_1$ so that the evanescent field is phase matched to the modes of ring cavity resonator 215.

Planar waveguide 210 coupling to ring cavity resonator 215 is adjusted by changing the gap $d_1$. Efficient coupling is achieved when the gap $d_1$ is on the order of the 1/e decay length of the confined electric field in planar waveguide 210. This is known as the impedance matched condition because the light round trip loss in ring cavity resonator 215 is equal to the coupling loss into ring cavity resonator 215 from planar waveguide 210. The largest finesse for ring cavity resonator 215 is not obtained by operating at the most efficient gap $d_1$. For larger gaps $d_1$, coupling efficiency plateaus as the maximum finesse of ring cavity resonator 215 is approached and weaker coupling is typically preferred as discussed above with respect to TIR cavity resonator 115. The finesse for ring cavity resonator 215 is typically selected to obtain optimum signal-to-noise for a chosen electronic detection scheme. The finesse is selected such that that the photn decay time or ring-down time matches the electronic detector bandwidth. Outcoupling from ring cavity resonator 215 to a detector (not shown) is typically accomplished by planar waveguide 211 whose coupling to ring cavity resonator 215 is adjusted by changing gap $d_2$. Alternatively, in other embodiments in accordance with the invention, both incoupling and outcoupling may be accomplished using planar waveguide 210 without waveguide 211. The electronic detector (not shown) measures the time dependence of the outcoupled signal which allows determination of the photon decay time.

Solutions for the electric field configuration for planar cavity ring-down spectrophotometer (CRDS) 200 may be obtained by numerically solving the wave equation for the electric field for the relevant configuration, such as the embodiment in accordance with the invention in FIG. 2a:

$$\nabla^2 \vec{E} + k^2 n^2(x,y,z)\vec{E} = 0 \qquad (7)$$

where the free space wave number, $k=2\pi/\lambda_0$ and the index of refraction n is a function of x, y, z.

FIG. 2b shows a side view of planar CRDS 200. The top portion of substrate 205 has been etched down and is coated with thin metal layer 245, typically silver or gold, to enable surface plasmon resonance formation. Similar to the discussion above for CRDS 100, a thin film containing a transducing layer (not shown), having a typical thickness of about 1 μm, is deposited onto thin metal layer 245. The photon decay rate or ring down time is first measured for CRDS 200 in the absence of the analyte or chemical to be detected. Analyte 250 is then deposited on the transducing layer (not shown) resulting in a change of the effective dielectric constant in the region above thin metal layer 245 if the substance of interest is present. The ring down time for CRDS 200 is modified by the change in the dielectric constant. The change in local dielectric constant effects the plasmon absorption coefficient resulting in a change in the value of the photon decay time $\tau(\omega)$. The substrate material beneath ring cavity resonator 245 is sufficiently thick to prevent evanescent coupling out the bottom of substrate 205 and any resulting effects on the ring down time.

The photon decay time for ring cavity resonator 215 differs from bulk optic TIR ring cavity resonator 115 above and is given by:

$$\tau(\omega) = \frac{t_r}{L_{bulk} + L_{surf} + L_{coupling} + L_{diff} + L_{bending} + L_{plasmon}} \quad (8)$$

where $t_r = 2\pi R n_r/c$ is the round trip time and $n_r$ is the index of refraction and R the radius of ring cavity resonator 215. Ring cavity resonator 215 loss is approximated by the sum of the roundtrip losses $L_i$.

For ring cavity resonator 215 fabricated from a highly transparent material, the loss per pass due to bulk attenuation is given by:

$$L_{bulk} = 2\alpha\pi R \quad (9)$$

where $\alpha$ is the bulk attenuation coefficient and R is the radius of ring cavity resonator 215.

The bending loss, $L_{bending}$, gives the loss due to the radius of curvature of ring cavity resonator 215 and is given by:

$$L_{bending} \approx \xi\left(\frac{a}{w}\right) e^{-\left(\frac{(w/a)^3 \lambda^2 R}{6\pi^2 n_r^2}\right)} \quad (10)$$

where $$\xi\left(\frac{a}{w}\right) = \left[\int_0^\infty \frac{E^2(r) r dr}{E^2(a/w)}\right]^{-1}$$

and $n_r$ is the refractive index of ring cavity resonator 215, $\alpha$ is the waveguide width, $\alpha/w$ is the transverse 1/e decay length of the waveguide electric field, w is the exponential decay constant and determines the decay rate of the electric field outside of waveguide 210, $\lambda$ is the wavelength of the incident light, R is the radius of ring cavity resonator 215 and E(r) is the electric field.

The diffraction loss $L_{diff}$ for ring cavity resonator 215, assuming region 3 effectively has infinite thickness, is given by:

$$L_{diff} \approx \frac{2}{a}\left[\frac{\kappa_2}{(\kappa_1 + \kappa_2)^2} + \frac{\kappa_3 + \kappa_3^*}{2|(\kappa_1 + \kappa_3)|^2}\right]\frac{\kappa_1^2}{\beta} \quad (11)$$

where $\kappa_i \approx \sqrt{(n_i^2 k^2 - \beta^2)}$ for i=1, 2, 3 and $\kappa_i$ is the wave number, $n_i$ is the effective index of refraction in region i (i=1, 2, 3) in FIG. 3, $$k = \frac{2\pi}{\lambda}$$

and $\beta$ is the propagation constant for the eigenmode of ring cavity resonator 215.

The coupling loss, $L_{coupling}$, for planar CRDS 200 is given by:

$$L_{coupling} = K\left(\frac{w}{a}d_i, n_i\right)\lambda^3 \propto \quad (12)$$
$$\iiint d^3 \vec{r}\left(\vec{E}_{waveguide\ 1}(\vec{r})\vec{E}_{resonator}^*(\vec{r}) + \vec{E}_{waveguide\ 2}(\vec{r})\vec{E}_{resonator}^*(\vec{r})\right)$$

where K is a geometric form factor depending on the electric field extent and the coupling length $d_i$, $\alpha$ is the waveguide width, $\alpha/w$ is the transverse 1/e decay length of the waveguide electric field and determines the decay rate of the electric field outside of waveguide 210, $d_i$(i=1, 2) is the distance between ring cavity resonator 215 and waveguide 210 or waveguide 211, respectively. From Eq. (12) it is apparent that the coupling loss increases strongly with wavelength because the transverse extent of the field increases and therefore the electric field overlap increases.

Planar CRDS 200, operating in the near infrared where $SiO_2$ has a bulk-loss $L_{bulk} \sim 5 \cdot 10^{-7}$/cm, allows absorption measurements less than $\sim 10^{-10}$ to be achieved as disclosed in Pipino et al. in "Evanescent wave cavity ring-down spectroscopy with a total-internal-reflection minicavity", in Reviews of Scientific Instruments, 68, 8, August 1997, p. 2978. For a discussion on how to construct ultra-high Q toroid microcavities see "Utra-high-Q toroid microcavity on a chip" by Armani et al. in NATURE, vol. 421, Feb. 27, 2003, p. 925, incorporated herein by reference. For a non-optimized example, take planar waveguide 210 and ring cavity resonator 215 to have a refractive index 0.3% different from substrate 205. Take planar waveguide 210 to have a cross-section of 8 µm by 8 µm adiabatically tapering to a cross-section of 3.6 µm by 3.6 µm, planar waveguide 211 to have a cross-section of 8 µm by 8 µm, ring cavity resonator 215 have a radius of 20 µm, substrate 205 to have a thickness of 24 µm, the distance between the top of substrate 205 and ring cavity resonator 215 to be 4 µm with a gap $d_1$=6.8 µm between planar waveguide 210 and ring cavity resonator 215 and a gap $d_2$=12.7 µm between planar waveguide 211 and ring cavity resonator 215. The finesse of the above configuration for CRDS 200 is about $1.2 \cdot 10^8$. Adding thin metal layer 245 as a 50 nm gold film reduces the finesse to about $2.5 \cdot 10^7$. Applying a transducing layer having a thickness of 1 µm and having $n_{refractive\ index}$=1.4 on thin metal layer 245, further lowers the finesse to about $2.1 \cdot 10^7$. For a transducing layer having a thickness of 1 µm and having $n_{refractive\ index}$=1.6, the cavity Q is lowered to about $9.8 \cdot 10^6$.

If both incoupling and outcoupling are performed by planar waveguide 210 and planar waveguide 211 is not present, the Q for CRDS 200 is about $2.0 \cdot 10^8$ using the values above. Adding thin metal layer 245 as a thin 50 nm gold film reduces the finesse to $4.2 \cdot 10^7$. Applying a transducing layer having a thickness of 1 µm and having $n_{refractive\ index}$=1.4 on thin metal layer 245, further lowers the cavity Q for CRDS 200 to about $3.4 \cdot 10^7$. For a transducing layer having a thickness of 1 µm and having $n_{refractive\ index}$=1.6, the cavity Q for CRDS 200 is lowered to about $2.7 \cdot 10^7$.

In both of the above examples, the cavity Q of CRDS 200, the combined cavity, metal and dielectric stack, is large enough to allow precision measurement of the photon decay time. For example, taking a cavity Q of $2.7 \cdot 10^7$ and an operational wavelength of 1550 nm, the corresponding photon decay time $\tau(\omega) = Q(\omega)/\omega \sim Q\lambda/2\pi c$ is about 20 nsec. With suitable averaging and signal processing, the fractional uncertainty in photon decay time $\Delta\tau/\tau$ may be reduced to about 0.5%. In this case, taking the bulk loss of $SiO_2$ to be about $10^{-7}$/cm at an operational wavelength of 1550 nm, the minimum detectable absorption is $\Delta\tau/\tau \cdot L_{bulk} \sim 10^{-10}$.

The presence of analyte 250 changes the local dielectric constant on top surface 249 of CRDS 200. The change in local dielectric constant effects the plasmon absorption coefficient resulting in a change in the value of the photon decay time $\tau(\omega)$ through $L_{plasmon}$. The photon decay rate or ring down time is first measured for CRDS 200 in the absence of the analyte or chemical to be detected but with thin metal layer 245 and the transducing layer present. The light from a tunable laser (not shown) excites a surface plasmon resonance and depending on the frequency, a certain fraction of the light is absorbed. The photon decay rate $\tau(\omega)$ of CRDS 200 and the finesse are inversely proportional to the fraction of light absorbed. Then top surface 249 of CRDS 200 is exposed to analyte 250, the chemical or biological agent to be sensed. As analyte 250 interacts with the transducing layer, the local dielectric constant is modified in the vicinity of the surface plasmon. This effects the nature of the surface plasmon: changes in the imaginary part of the dielectric constant change the plasmon absorption. If more light is absorbed in the presence of analyte 250 leading to a decrease in the value of $\tau(\omega)$. The difference between the photon decay time in the absence and presence of analyte 250 is proportional to the concentration of analyte 250 through the plasmon loss term of Eq. (5). The change in the surface plasmon resonance coefficient in the presence of analyte 250 may be mapped as a function of frequency of the tunable laser in analogy to the discussion above with reference to FIG. 1b.

While the invention has been described in conjunction with specific embodiments, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

The invention claimed is:

1. A cavity ring-down spectrophotometer comprising:
   an optical cavity resonator having a first surface; and
   a thin metal layer disposed on said first surface, said thin metal layer operable to receive a transducing layer.

2. The apparatus of claim 1 further comprising a tunable coherent light source evanescently coupled to said optical cavity resonator.

3. The apparatus of claim 2 wherein said tunable coherent light source is evanescently coupled to said optical cavity resonator using a prism.

4. The apparatus of claim 1 wherein said optical cavity resonator has a polygonal shape.

5. The apparatus of claim 4 wherein a face of said polygonal shape comprises said first surface.

6. The apparatus of claim 4 wherein said polygonal shape is a square.

7. The apparatus of claim 1 wherein said optical cavity resonator has a toroidal shape and is embedded within a substrate.

8. The apparatus of claim 7 wherein a planar face of said toroidal shape comprises said first surface.

9. The apparatus of claim 7 further comprising a first waveguide disposed in said substrate proximate to said optical cavity resonator operable such that optical energy in said first waveguide is evanescently coupled into said optical cavity resonator.

10. The apparatus of claim 9 further comprising a second waveguide disposed in said substrate proximate to said optical cavity resonator operable such that optical energy in said cavity resonator is evanescently outcoupled into said second waveguide.

11. The apparatus of claim 9 further comprising a tunable coherent light source for introducing light into said first waveguide.

12. The apparatus of claim 1 wherein said transducing layer is operable to receive an analyte.

13. The apparatus of claim 1 wherein said optical cavity resonator is comprised of $SiO_2$.

14. The apparatus of claim 9 wherein said first waveguide is adiabatically tapered to improve evanescent coupling to said optical cavity resonator.

15. The apparatus of claim 2 further comprising a heterodyne based detector optically coupled to said optical cavity resonator for coherent detection of weak signals.

16. The apparatus of claim 1 wherein said optical cavity resonator is superpolished to achieve a high quality factor.

17. A method for making a cavity ring-down spectrophotometer comprising:
   providing an optical cavity resonator having a first surface; and
   depositing a thin metal layer on said first surface, said thin metal layer operable to receive a transducing layer.

18. The method of claim 17 further comprising providing tunable coherent light source evanescently coupled to said optical cavity resonator.

19. The method of claim 17 wherein said optical cavity resonator has a toroidal shape and is embedded within a substrate.

20. The method of claim 19 further comprising providing a first waveguide disposed in said substrate proximate to said optical cavity resonator operable such that optical energy in said first waveguide is evanescently coupled into said optical cavity resonator.

* * * * *